United States Patent
Tatsumi

(10) Patent No.: US 7,175,812 B2
(45) Date of Patent: Feb. 13, 2007

(54) AUTOMATIC SAMPLER AND NEEDLE FOR THE SAME

(75) Inventor: Nobuyuki Tatsumi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 471 days.

(21) Appl. No.: 10/056,136

(22) Filed: Jan. 24, 2002

(65) Prior Publication Data

US 2002/0102185 A1   Aug. 1, 2002

(30) Foreign Application Priority Data

Jan. 31, 2001   (JP) .............................. 2001-022663

(51) Int. Cl.
    *B01L 3/02* (2006.01)
(52) U.S. Cl. .................... 422/100; 73/863.32; 73/864; 604/44; 604/187
(58) Field of Classification Search ................ 422/100, 422/99; 604/44, 187
See application file for complete search history.

(56) References Cited

U.S. PATENT DOCUMENTS

| | | | | | |
|---|---|---|---|---|---|
| 3,883,305 | A | * | 5/1975 | Hoskins et al. ................ 422/65 |
| 3,915,677 | A | * | 10/1975 | Oppegaard ................ 73/864.86 |
| 3,949,751 | A | * | 4/1976 | Birch et al. ............. 128/203.15 |
| 4,309,912 | A | * | 1/1982 | Smith ...................... 73/864.72 |
| 4,404,862 | A | * | 9/1983 | Harris, Sr. ............... 73/864.16 |
| 4,558,588 | A | * | 12/1985 | Beaudoin et al. .......... 73/54.25 |
| 4,582,060 | A | * | 4/1986 | Bailey ........................ 606/186 |
| 4,708,782 | A | * | 11/1987 | Andresen et al. ........ 210/198.2 |
| 4,781,198 | A | * | 11/1988 | Kanabrocki ................. 600/431 |
| 4,945,640 | A | * | 8/1990 | Garg et al. .................... 30/350 |
| 4,946,651 | A | * | 8/1990 | Liston et al. ................ 422/102 |
| 5,012,845 | A | * | 5/1991 | Averette ..................... 141/329 |
| 5,171,530 | A | * | 12/1992 | Pennatto ....................... 422/63 |
| 5,183,043 | A | * | 2/1993 | Band et al. .................. 600/376 |
| 5,223,226 | A | * | 6/1993 | Wittmer et al. ............. 422/100 |
| 5,354,537 | A | * | 10/1994 | Moreno ....................... 422/100 |
| 5,372,782 | A | * | 12/1994 | Karkantis et al. ............. 422/63 |
| 5,391,499 | A | * | 2/1995 | Karkantis et al. ........... 436/180 |
| 5,468,452 | A | * | 11/1995 | Hagiwara ..................... 422/70 |
| 5,468,453 | A | * | 11/1995 | Holt et al. ................... 422/100 |
| 5,637,399 | A | * | 6/1997 | Yoshikawa et al. ......... 428/369 |
| 5,789,252 | A | * | 8/1998 | Fujita et al. .................. 436/49 |
| 5,820,622 | A | * | 10/1998 | Gross et al. ............. 604/890.1 |
| 5,843,378 | A | * | 12/1998 | El-Hage et al. ............. 422/100 |
| 5,866,004 | A | * | 2/1999 | Houck et al. ................ 210/634 |
| 5,879,949 | A | * | 3/1999 | Cole et al. ................... 436/173 |
| 5,938,604 | A | * | 8/1999 | Wagner et al. .............. 600/436 |
| 5,954,954 | A | * | 9/1999 | Houck et al. ............. 210/198.2 |
| 5,997,517 | A | * | 12/1999 | Whitbourne ................ 604/265 |
| 6,117,394 | A | * | 9/2000 | Smith ......................... 422/100 |

(Continued)

*Primary Examiner*—Brian R. Gordon
(74) *Attorney, Agent, or Firm*—Rankin, Hill, Porter & Clark LLP

(57) ABSTRACT

The surface of a needle for collecting samples is coated with a coating material lower in chemical activity than a base metal of the needle. More specifically, the surface of the needle may be coated with a layer of gold or platinum. Alternatively, the surface of the needle may be coated with a synthetic resin coating of, for example, PEEK which is superior in chemical resistance. As a result, it is possible to obtain a practically sufficient antifouling effect even on contamination coming from chemical adsorption. Such contamination could not be removed sufficiently only by related-art measures against physical contamination. Thus, it is possible to provide an automatic sampler which can perform highly sensitive analysis.

3 Claims, 4 Drawing Sheets

U.S. PATENT DOCUMENTS

| | | | |
|---|---|---|---|
| 6,132,582 A * | 10/2000 | King et al. | 204/604 |
| 6,135,993 A * | 10/2000 | Hussman | 606/2 |
| 6,148,666 A * | 11/2000 | Roesicke | 73/290 R |
| 6,306,176 B1 * | 10/2001 | Whitbourne | 623/23.59 |
| 6,350,273 B1 * | 2/2002 | Minagawa et al. | 606/186 |
| 6,365,024 B1 * | 4/2002 | Li et al. | 204/604 |
| 6,368,392 B1 * | 4/2002 | Ohtake et al. | 96/65 |
| 6,455,316 B1 * | 9/2002 | Turner et al. | 436/37 |
| 6,475,391 B2 * | 11/2002 | Safir et al. | 210/656 |
| 6,482,362 B1 * | 11/2002 | Smith | 422/100 |
| 6,539,410 B1 * | 3/2003 | Klass | 708/255 |
| 6,599,276 B1 * | 7/2003 | Humphrey | 604/272 |
| 6,638,259 B1 * | 10/2003 | Palasis et al. | 604/264 |
| 6,715,693 B1 * | 4/2004 | Dam et al. | 239/88 |
| 6,733,728 B1 * | 5/2004 | Mimura et al. | 422/65 |
| 6,793,632 B2 * | 9/2004 | Sohrab | 600/573 |
| 6,837,884 B2 * | 1/2005 | Woloszko | 606/32 |
| 6,899,708 B2 * | 5/2005 | Speck et al. | 606/15 |
| 7,055,402 B2 * | 6/2006 | Staples et al. | 73/864.21 |
| 2002/0072706 A1 * | 6/2002 | Hiblar et al. | 604/101.01 |
| 2002/0150511 A1 * | 10/2002 | Wiktor | 422/100 |
| 2002/0155620 A1 * | 10/2002 | Hutchens et al. | 436/173 |
| 2002/0168778 A1 * | 11/2002 | Andrien et al. | 436/173 |
| 2003/0013201 A1 * | 1/2003 | Sklar et al. | 436/63 |
| 2003/0014047 A1 * | 1/2003 | Woloszko et al. | 606/41 |
| 2003/0014051 A1 * | 1/2003 | Woloszko | 606/46 |
| 2003/0131031 A1 * | 7/2003 | Klass | 708/250 |
| 2003/0171760 A1 * | 9/2003 | Gambale | 606/139 |
| 2003/0233065 A1 * | 12/2003 | Steward et al. | 604/22 |
| 2004/0087933 A1 * | 5/2004 | Lee et al. | 604/532 |
| 2005/0017099 A1 * | 1/2005 | Batich et al. | 239/589 |
| 2005/0217393 A1 * | 10/2005 | Tomita et al. | 73/864.41 |

* cited by examiner

VIAL NO. = 20  INJECTION AMOUNT : 2

DETECTOR A(260nm)

| PEAK NUMBER | RETENTION TIME | AREA | HEIGHT |
|---|---|---|---|
| 6 | 5.382 | 39637446 | 1981953 |

VIAL NO. = 70  INJECTION AMOUNT : 2

DETECTOR A(260nm)

| PEAK NUMBER | RETENTION TIME | AREA | HEIGHT |
|---|---|---|---|
| 1 | 4.725 | 627 | 26 |
| 2 | 5.469 | 9340 | 463 |

VIAL NO. = 10    INJECTION AMOUNT : 2

| DETECTOR B(260nm) | RETENTION TIME | AREA | HEIGHT |
|---|---|---|---|
| | 6.525 | 48126387 | 2067405 |

VIAL NO. = 40    INJECTION AMOUNT : 2

| DETECTOR B(260nm) | RETENTION TIME | AREA | HEIGHT |
|---|---|---|---|
| | 6.653 | 321 | 22 |

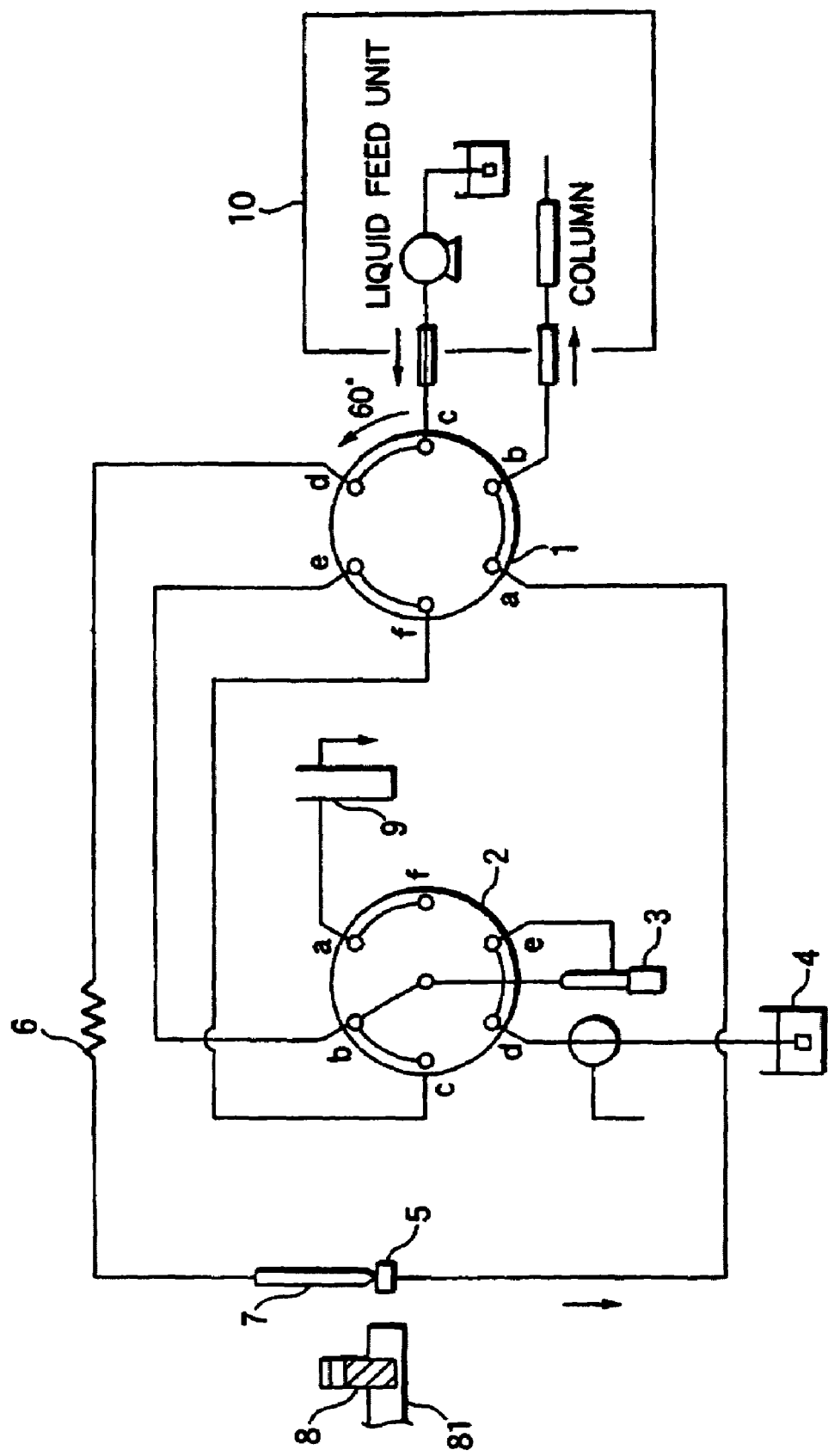

AUTOMATIC SAMPLER AND NEEDLE FOR THE SAME

BACKGROUND OF THE INVENTION

1. Field of the Invention

The present invention relates to an automatic sampler and a needle of the automatic sampler for an analyzer which performs liquid analysis, such as a liquid chromatograph. More particularly, the needle is subject to a surface treatment or coating which reduces contamination of the needle caused by chemical adsorption.

2. Description of the Related Art

FIG. 4 shows an example of a main portion of a flow path arrangement of an automatic sampler for a liquid chromatograph.

In the automatic sampler shown in FIG. 4, a plunger 3 is designed to perform a reciprocating motion by mechanical force. A liquid sample to be analyzed is stored in a large number of vials (small-volume sample bottles) 8 in advance. The vials 8 are arranged on a rack 81. A needle 7 collects samples from the vials 8. The needle 7 is connected to an injector valve 1 through a looped flexible pipe (hereinafter referred to as "loop") 6. In addition, the needle 7 is retained by a not-shown drive mechanism so that the needle 7 can move freely among the vials 8, a rinse port 9, and an injection port 5 in accordance with input from, for example, programmed instructions. A valve 2 is a six-position rotary valve with six ports "a" to "f" for switching a flow path of liquid sucked and discharged by the plunger 3. The reference numeral 4 represents a rinse bottle.

The injector valve 1 is connected to a liquid chromatograph apparatus 10 through pipes so as to introduce a liquid sample into a flow path of mobile phase liquid in the liquid chromatograph apparatus 10.

An example of an operational sequence of the sample suction and sample injection processes using an auto-injector as shown in FIG. 4 is as follows.

(1) At sample suction, the valve 2 is switched to communicate port b with port 0, and the injector valve 1 is switched to communicate port d with port e and port b with port c, respectively. At the sample suction position, the needle 7 is dipped into a vial 8, and the plunger 3 is driven to suck a predetermined quantity of liquid sample from the vial 8 into the loop 6 through the needle 7. The sucked liquid sample is collected in the loop 6 so as not to reach the valve 2 or the plunger 3.

(2) Next, the needle 7 is pulled out from the vial 8 and moved to the injection port 5 as shown in FIG. 4.

(3) The injector valve 1 is then switched to communicate port a with port b and port e with port f respectively, as shown in FIG. 4, thereby introducing the sample in the loop 6 into the flow path of the mobile phase liquid. Thus, analysis of the liquid chromatograph is started.

(4) After the needle 7 is moved to a vial 8 containing a sample to be analyzed next, operations (1) through (3) are repeated.

In the automatic sampler as described above, a step of rinsing the needle 7 is necessarily included after any sample is sampled. The rinsing step is very important to avoid mixing a preceding sample into another sample to be analyzed (cross contamination).

In the related art, mainly measures against physical contamination have been taken to prevent cross contamination produced through the intermediation of the needle 7. For example, the needle 7 was rinsed, or the surface of the needle 7 was polished and smoothed to help prevent dirt from adhering thereto. However, contamination of the needle 7 is not limited to only physical contamination.

More specifically, stainless steel is commonly used as a material for making the needle 7. Stainless steel is an alloy with an iron base. Therefore, iron is exposed on the surface of stainless steel microscopically, and accordingly, some amount of sample component is adsorbed on the iron portion of the stainless steel due to the chemical properties of iron. For example, a chemically adsorptive phenomenon is easily produced in basic matter because its hydroxyl group is attracted to iron on the surface of stainless steel. The sample component once adsorbed chemically cannot be removed easily, even if it is vigorously rinsed with organic-solvent-based detergent. Such a sample component adsorbed on the surface of the needle 7 and remaining after rinsing is partially mixed into the next sample to be analyzed. Thus, cross contamination is, though slightly in some cases, brought about.

Such cross contamination caused by chemical adsorption has heretofore been substantially overlooked. In recent years, however, with advances in analytic sensitization, it has become necessary to take effective measures against even slight cross contamination.

SUMMARY OF THE INVENTION

The present invention was developed in consideration of the drawbacks associated with the related art. It is an object of the invention to provide an automatic sampler and a needle for the automatic sampler in which contamination, caused by chemical adsorption and still remaining after measures against physical contamination are taken on the surface of the needle, is restrained so that the automatic sampler can perform highly sensitive analysis.

In order to attain the foregoing object, an automatic sampler according to the present invention comprises a needle which is subject to a surface treatment for reducing chemical adsorption. More specifically, the needle of the present invention contains a base metal, and the surface of the needle is coated with a coating material which is lower in chemical activity than the chemical activity of the base metal of the needle. In one embodiment, the surface of the needle is plated with a noble metal, such as gold or platinum. Alternatively, the surface of the needle may be coated with synthetic resin such as PEEK which is superior in chemical resistance. Further, a quartz thin film may be formed on the surface of the needle. Moreover, a non-noble metal may be plated or deposited on the surface of the needle. The automatic sampler of the present invention is preferably used for a liquid chromatography. It is possible to obtain a practically sufficient antifouling effect, even against contamination coming from chemical adsorption which cannot be removed sufficiently by related-art measures against physical contamination. Thus, it is possible to provide an automatic sampler which can perform highly sensitive analysis.

BRIEF DESCRIPTION OF THE DRAWINGS

FIG. 4 is a diagram showing an example of a main portion of a flow path of an automatic sampler for a liquid chromatograph.

DETAILED DESCRIPTION OF THE INVENTION

Figure 1A:
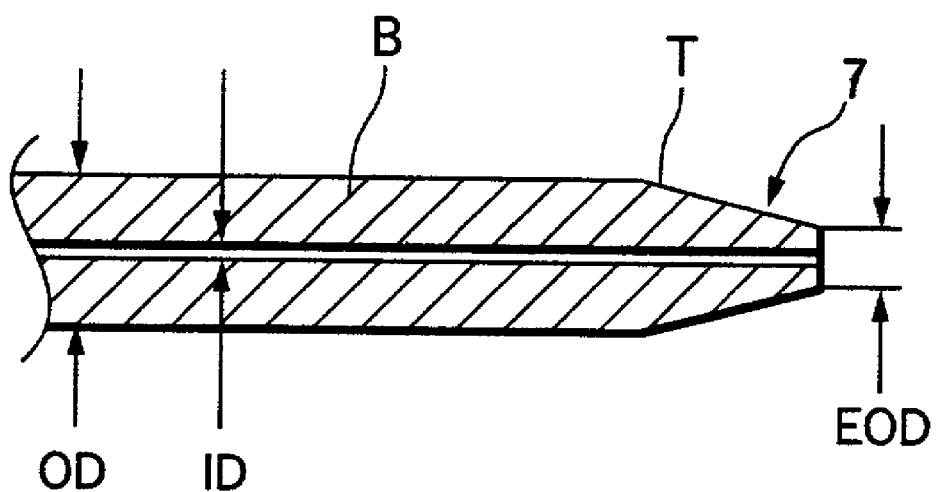
FIG. 1A is a diagram showing a needle according a first embodiment of the present invention.
Figure 1B:
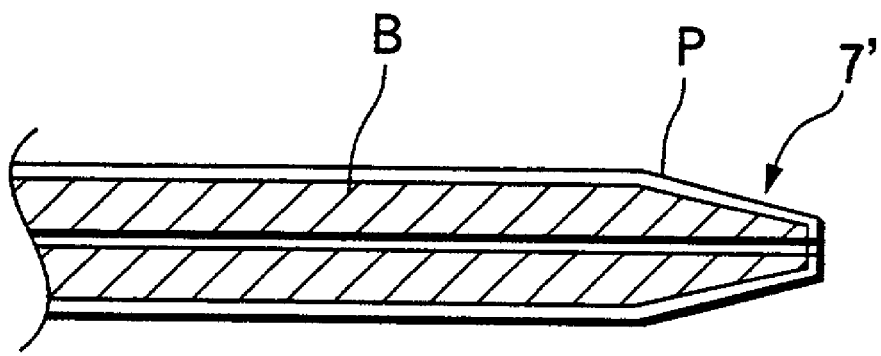
FIG. 1B is a diagram showing a needle according to a second embodiment of the present invention.

FIGS. 1A and 1B show needles according to first and second embodiments of the invention, respectively.

The needle 7 shown in FIG. 1A is a flat-head needle with an outer diameter OD of 1.2 mm and an inner diameter ID of 0.5, and a flat end with an outer diameter EOD of 0.65 mm. Base metal B is a stainless steel, and the surface of the base metal B is coated with a platinum-plated layer T having a thickness of several micrometers (μm). The surface of the needle is covered with the platinum-plated layer T which is much lower in adsorptive activity than stainless steel. Therefore, when the needle 7 is used for the automatic sampler shown in FIG. 4, chemical adsorption on the surface of the needle 7 is restrained, which in turn reduces cross-contamination.

In the needle 7' shown in FIG. 1B, base metal B is coated with a synthetic resin coating P (about 300 μm thick) instead of the metal plating used in the first embodiment. The synthetic resin coating P in this second embodiment is made of PEEK (polyetheretherketone) which is a synthetic resin having high chemical resistance and mechanical strength. As the coating method for the synthetic resin, a powder coating method can be applied. When using the synthetic resin, the dimensions of the base metal B may have to be made somewhat small in advance consideration of the thickness of the synthetic resin coating P.

In particular, PEEK is an organic material, and accordingly, hardly shows a chemical adsorptive property. In addition, PEEK shows superior resistance to various chemicals, and is therefore also used as a material for piping in a liquid chromatograph. Thus, PEEK is preferably used for the needle 7' in the automatic sampler for the liquid chromatograph.

FIGS. 2A and 2B and FIGS. 3A and 3B are graphs of experimental data showing the cross contamination effect when the needle 7 is left uncoated, and a reduction of the cross-contamination effect when the needle is coated with a platinum-plated layer T.

In these experiments, a sample was analyzed which included a solution of a strong basic chlorhexidine hydrochloride diluted with a liquid. The liquid used was the same as the mobile phase liquid used in the liquid chromatograph. An area A of a peak obtained by analyzing this sample was calculated. Subsequently, after rinsing the needle, only the mobile phase liquid (a blank sample) was analyzed so that an area B of a peak appearing for the same retention time was measured. The degree of cross contamination was expressed by a ratio C (%) of B to A.

Figure 2A:
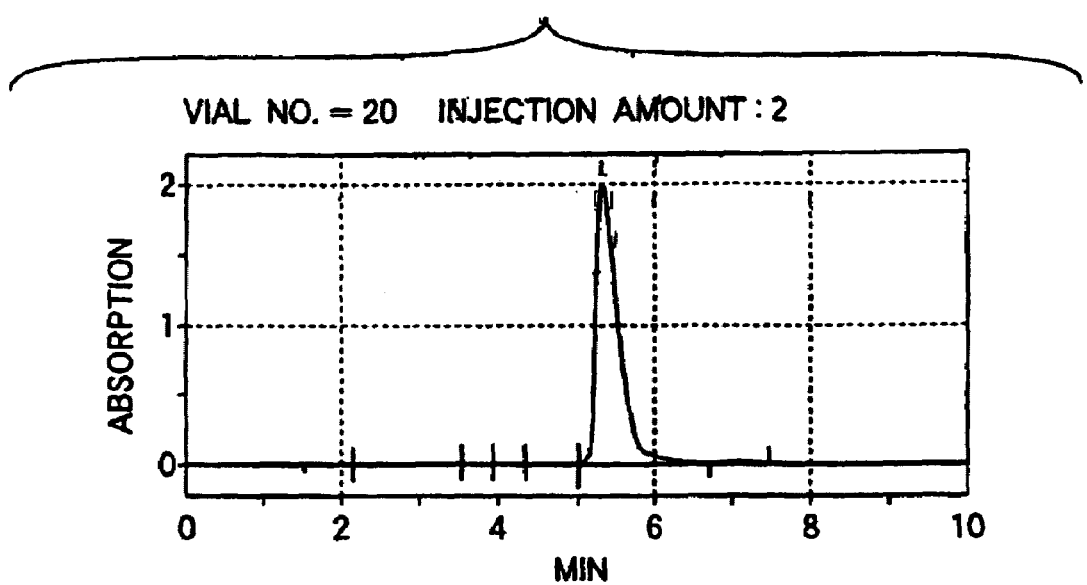
FIGS. 2A and 2B are graphs of experimental data showing the result of analysis of a chlorhexidine hydrochloride solution and a blank sample in the case where a related-art needle made of stainless steel alone was used.
Figure 2B:
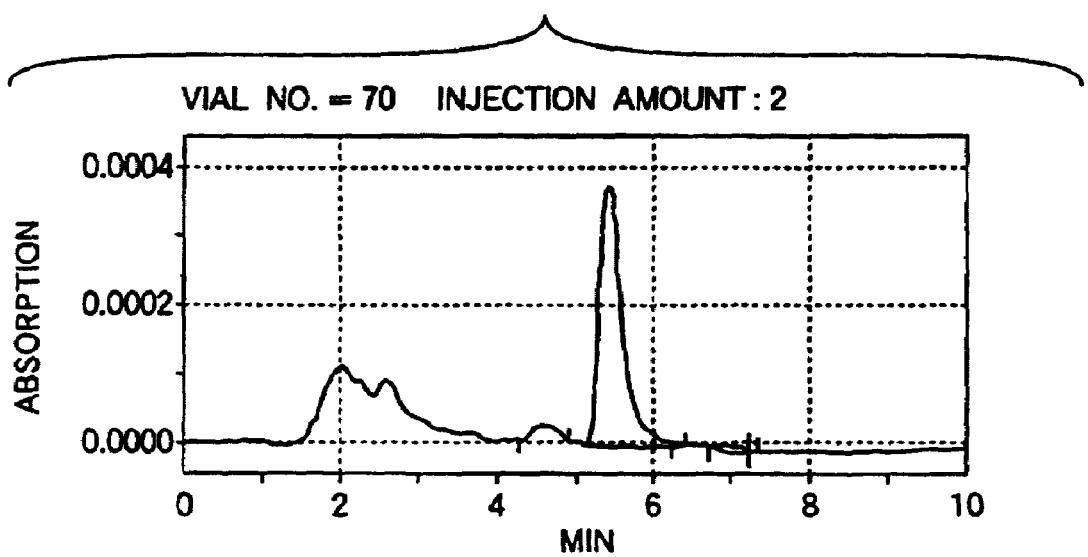

FIGS. 2A and 2B show the case where a related-art needle made of stainless steel alone was used. FIG. 2A shows the result of analysis of the chlorhexidine hydrochloride solution, and FIG. 2B shows the result of analysis of the blank sample carried out following the analysis in FIG. 2A. From respective area values, cross contamination C is calculated by:

$$C=9340/39637446=0.024\%$$

Figure 3A:
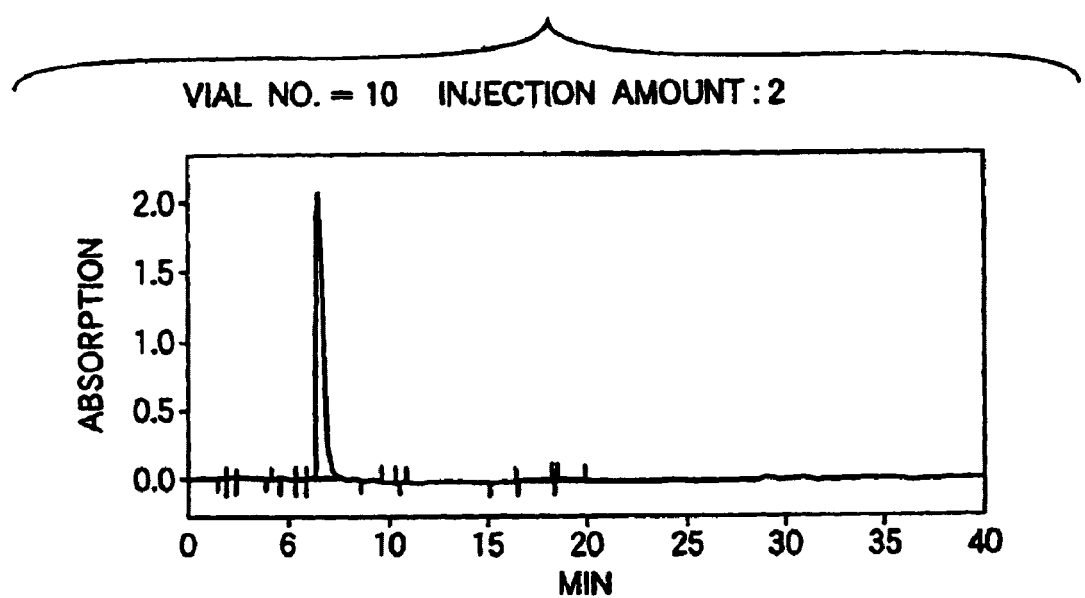
FIGS. 3A and 3B are graphs of experimental data showing the result of analysis of a chlorhexidine hydrochloride solution and a blank sample in the case where a needle coated with the platinum-plated layer T according to the present invention was used.
Figure 3B:
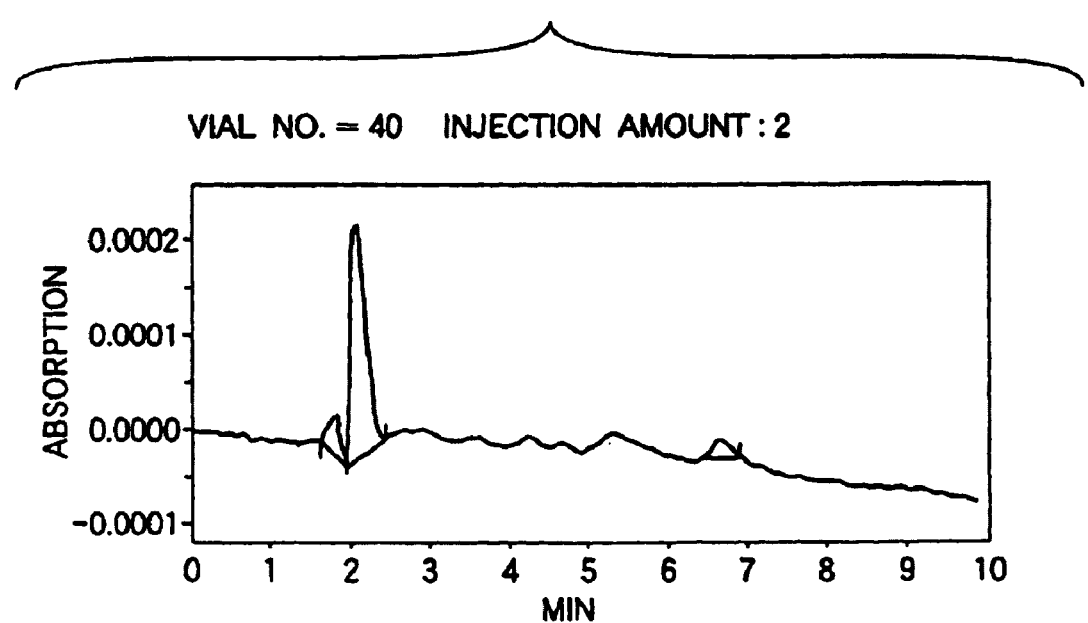

Next, FIGS. 3A and 3B show the results of analysis in the case where the needle 7 coated with the platinum-plated layer T was used. Cross contamination C in this case is calculated by:

$$C=321/49126387=0.00065\%$$

From these results, it can be understood that the degree of cross contamination is reduced to about 1/40 when the needle 7 is coated with the platinum-plated layer T, and a remarkable improvement effect can therefore be obtained.

The setting conditions of the liquid chromatograph in these experiments was as follows.

mobile phase: 100 mM perchloric acid contianing phosphoric acid buffer (pH 2.6): acetonitrile=55:45 flow rate: 0.2 mL/min column: VP-ODS φ2 mm×150 mm (means a diameter)

oven temperature: 40° C.

detector: UV 260 nm sample: chlorhexidine hydrochloride (12 mg of which is diluted with mobile phase of 10 mL)

injection amount: 2 μL

According to the present invention, the surface of the needle 7, 7' is covered with a coating material lower in chemical activity than the base metal B of the needle 7, 7'.

Of course, the coating material is not limited to the embodiments described herein. For example, when the base metal B is plated with a noble metal such as any other element of the platinum group or gold in place of platinum, it is possible to obtain an effect equal to or close to that in the case of platinum. In addition, when the base metal B is plated with a non-noble metal such as nickel or chromium which are lower in chemical activity than iron, a deserved improvement effect can be expected, though it comes short of that in the case where the base metal B is plated with noble metal.

In addition, PFE (polyfluorethylene), or PE (polyethylene) may be used in place of PEEK as the synthetic resin coating P. In this case, an effect corresponding to the properties of such a raw material can be expected.

In the embodiments described above, only the outer surface of the needle 7, 7' is covered with a coating material, but the inner surface of the needle 7, 7' is not coated. Therefore, there may be concern that the inner surface of the needle would remain as a cause of cross contamination. However, the surface area of the inner surface is smaller than 20% of the total surface area of the needle 7, 7', and hence, the influence of the inner surface is not very significant. In addition, the inner surface of the needle 7, 7' can be rinsed efficiently if the pressure and flow rate of the rinse are increased. Thus, the influence of the metal surface of the inner surface on cross-contamination is limited to an ignorable extent.

Notwithstanding the small influence of the inner surface of the needle and the improved methods for rinsing, to further reduce cross contamination, it is desired that the inner surface of the needle 7, 7' also be coated with an inactive material.

With a chemical vapor deposition method (CVD) already known as a method for coating the inner surface of a capillary, a metallic thin film can additionally be formed on the inner surface of the needle 7, 7'. In addition, the inactive material is not limited to metal, but a thin film of high-purity quartz or other material may be formed. Coating an inner wall of a capillary with a quartz thin film is a method put into practical use for treating the inner surface of a column in a gas chromatograph. High-purity quartz is extremely low in adsorptive activity so that contamination can be reduced to the utmost extent by this treatment.

The needle 7, 7' according to the present invention can be applied to any automatic sampler of such a type that liquid samples are sampled sequentially from a plurality of vials 8 through the needle 7, 7', including the automatic sampler shown in FIG. 4. In addition, the needle 7, 7' maybe applied broadly to not only automatic samplers for liquid chromatographs, but also automatic samplers for various analyzers aimed at performing liquid analysis. Further, the needle may be applied whenever there is reason for disinfecting the needle for continued use rather than disposing of the needle.

Incidentally, the numerical values of the dimensions shown in FIGS. 1A and 1B are shown by way of example and as such, the invention is not limited to such values. In addition, the material of the base metal B of the needle 7, 7' is not limited to stainless steel.

As described above in detail, the present invention pays attention to the fact that contamination still remains after a needle is rinsed or polished due to chemical adsorption. In order to solve the problem, the present invention uses a coating material low in chemically adsorptive activity which is applied to the surface of the needle. When the automatic sampler according to the present invention is combined with a liquid chromatograph, disturbance due to cross contamination is eliminated so that analysis can be made highly sensitive.

While the presently preferred embodiments of the present invention have been shown and described, it is to be understood that the disclosures are for the purpose of illustration and that various changes and modifications may be made without departing from the scope of the invention as set forth in the appended claims.

What is claimed is:
1. An automatic sampler comprising:
a plurality of sample vessels; and
a needle for collecting liquid samples sequentially from the sample vessels, said needle containing a non-noble base metal and having an outer surface coated with a first coating material that has a chemical activity lower than a chemical activity of the base metal of said needle, wherein said first coating material includes a noble metal including platinum, a platinum group metal, or gold that is plated or deposited on said needle, and wherein a second coating material comprising a quartz thin film is formed on an inner surface of said needle by a chemical vapor deposition method.
2. An instrument comprising:
an automatic sampler including:
a plurality of sample vessels; and
a needle for collecting liquid samples sequentially from the sample vessels, said needle containing a non-noble base metal and having an outer surface and an inner surface, the inner surface defining a flow path for the liquid samples collected from the sample vessels, wherein only the outer surface of the needle is coated with a coating material that includes a synthetic resin coating including polyetheretherketone, and wherein the inner surface of the needle is coated via a chemical vapor deposition method with either a metallic thin film or a thin film of high-purity quartz, and
wherein the instrument further comprises a liquid analysis apparatus for receiving the liquid samples collected by the needle.
3. The instrument according to claim 2, further comprising:
a rinsing means for rinsing the needle after collecting the liquid samples.

* * * * *